(12) United States Patent
Ozaki

(10) Patent No.: US 6,589,030 B2
(45) Date of Patent: Jul. 8, 2003

(54) MAGNETICALLY LEVITATED PUMP APPARATUS

(75) Inventor: Takayoshi Ozaki, Iwata (JP)

(73) Assignees: NTN Corporation, Osaka (JP); Terumo Kabushiki Kaisha, Tokyo (JP)

(*) Notice: Subject to any disclaimer, the term of this patent is extended or adjusted under 35 U.S.C. 154(b) by 210 days.

(21) Appl. No.: 09/883,221

(22) Filed: Jun. 19, 2001

(65) Prior Publication Data

US 2001/0053330 A1 Dec. 20, 2001

(30) Foreign Application Priority Data

| Jun. 20, 2000 | (JP) | 2000-184410 |
| Jun. 20, 2000 | (JP) | 2000-184411 |
| Jul. 10, 2000 | (JP) | 2000-207835 |
| Jul. 10, 2000 | (JP) | 2000-207837 |

(51) Int. Cl.$^7$ ............................................. F04B 17/00
(52) U.S. Cl. ........................................ 417/420; 417/44.1
(58) Field of Search .................... 417/420, 44.1, 417/45, 410.1, 423.4, 423.7, 423.12; 415/230, 900; 600/3, 16, 151; 327/552, 556

(56) References Cited

U.S. PATENT DOCUMENTS

| 4,688,998 A | * | 8/1987 | Olsen et al. ................. 417/356 |
| 5,725,357 A | * | 3/1998 | Nakazeki et al. .............. 417/18 |
| 5,911,558 A | * | 6/1999 | Nakazeki et al. ............ 415/118 |
| 6,015,275 A | * | 1/2000 | Suzuki et al. ........... 417/423.12 |
| 6,129,660 A | * | 10/2000 | Nakazeki et al. .............. 600/17 |
| 6,259,178 B1 | * | 7/2001 | Suzuki et al. ............... 310/90.5 |
| 6,264,635 B1 | * | 7/2001 | Wampler et al. ............. 604/151 |
| 6,368,075 B1 | * | 4/2002 | Fremerey ..................... 417/365 |
| 6,394,769 B1 | * | 5/2002 | Bearnson et al. ........ 417/423.7 |
| 6,398,524 B1 | * | 6/2002 | Taira et al. .................. 417/398 |
| 6,435,847 B2 | * | 8/2002 | Kubo et al. .............. 417/423.4 |
| 6,468,041 B2 | * | 10/2002 | Ozaki ......................... 417/44.1 |
| 6,527,699 B1 | * | 3/2003 | Goldowsky .................. 600/16 |

* cited by examiner

Primary Examiner—Teresa Walberg
Assistant Examiner—Vinod D. Patel
(74) Attorney, Agent, or Firm—McDermott, Will & Emery

(57) ABSTRACT

A power supply feeds a dc voltage to an operational amplifier at an inverting input while a motor current command value is input to the operational amplifier at a non-inverting input and when a dc voltage being supplied to a power amplifier varies the operational amplifier responds to the voltage variation by adjusting the motor current command value to alter a control signal applied to a motor control circuit and thus reduce revolution-rate variation.

17 Claims, 12 Drawing Sheets

CROSS SECTION ALONG IB-IB

US 6,589,030 B2

MAGNETICALLY LEVITATED PUMP APPARATUS

BACKGROUND OF THE INVENTION

1. Field of the Invention

The present invention relates to fluid pump apparatus and more specifically to those magnetically levitating an impeller to discharge fluid such as blood.

2. Description of the Background Art

FIG. 18 is a vertical cross section of a magnetically levitated (maglev) pump apparatus and a block diagram of a controller thereof. In FIG. 18 a maglev pump apparatus 100 is configured with an electromagnet unit 120, a pump unit 130 and a motor unit 140 housed in a cylindrical housing 101. Electromagnet unit 120 has an electromagnet 121 and a position sensor 122 incorporated therein. Housing 101 has on one side a side wall having a center provided with an inlet 102 introducing a fluid. At least three electromagnets 121 and at least three position sensors 122 surround inlet 102.

In pump unit 130 an impeller 131 is rotatably housed and it has a portion closer to electromagnet unit 120, or closer to one side, that is supported by electromagnet 121 contactless through a partition 103, and position sensor 122 senses the distance as measured from one side of impeller 131. Impeller 131 has the other side with a permanent magnet 132 buried therein. Motor unit 140 houses a motor 141 and a rotor 142. Rotor 142 has a surface facing pump unit 130 and having a permanent magnet 143 buried therein opposite to permanent magnet 132 of impeller 131 with a partition 104 posed therebetween.

In the maglev pump apparatus thus configured, position sensor 122 provides an output which is in turn input to a sensor circuit 301 included in a controller 300 and sensor circuit 301 detects the distance between one side of impeller 131 and position sensor 122. Sensor circuit 301 provides an output which is in turn input to a PID compensator 302 to provide PID compensation and PID compensator 302 provides an output which is in turn amplified by a power amplifier 303 and thus applied to electromagnet 121 to control attractive force exerted toward the opposite side of impeller 131.

Furthermore impeller 131 has a portion closer to motor unit 140 that is affected by the attractive force exerted by permanent magnets 132 and 143 and impeller 131 is magnetically levitated by a non-controlled bearing provided by permanent magnets 132 and 143 and a controlled bearing provided by electromagnet 121 and it is rotated by the driving force of a motor 141 to allow blood or any other similar fluid introduced through inlet 102 to be output through an outlet (not shown) formed at pump unit 130.

In the FIG. 18 maglev pump 100 when a command is issued to provide levitation via the magnetic bearing, i.e., when attractive force occurs at electromagnet 121, as shown FIG. 19, impeller 13 moves from a position A, corresponding to an internal wall surface closer to motor 140 affected by a significant attractive force created by permanent magnets 132 and 143 configuring magnetic-coupling, to a normal levitation position B. However, because of over-shoot of an excessive response as impeller 131 levitates, impeller 131 exceeds normal position B and impinges against a position C corresponding to an internal wall surface closer to electromagnet unit 120, as represented in FIG. 19. Thereafter impeller 131 moves to normal levitation position B. If impeller 131, a target of position sensor 122, impinges on a wall surface and have its surface damaged, the sensing function may be impaired.

Furthermore if the apparatus is used as a blood pomp impeller 131 is housed in pump unit 130 having its inner wall surface coated with heparin to prevent formation of thrombosis and if impeller 131 impinges against the inner wall of the pump chamber the coating would be disadvantageously peeled off.

SUMMARY OF THE INVENTION

Therefore a main object of the present invention is to provide a maglev pump capable of preventing an impeller from impinging against an inner wall of a pump chamber when a command is issued to provide magnetic levitation.

The present invention provides a maglev pump including: a pump unit outputting a fluid through revolution of a rotative member in a casing; a drive unit magnetically coupled with the rotative member without contacting the rotative member, to rotate the rotative member; a position detection unit detecting a position of the rotative member as the rotative member levitates; and a controlled magnetic bearing unit operative in response to an output of the position detection unit to support the rotative member without contacting the rotative member, and it is characterized in that it is provided with a control means controlling a command signal of the controlled magnetic bearing unit to allow the rotative member to have a position closer to the drive unit when the rotative member starts magnetic levitation.

Thus in the present invention the rotative member can be prevented from impinging against an internal wall of the housing when a command is issued to provide magnetic levitation. Thus the internal wall of the housing can be protected from damage.

Preferably in magnetic levitation the control means shifts the signal output of the position detection unit gradually to a normal value.

More preferably the control means gradually shifts the signal output from the position detection unit in a direction opposite to a normal value to terminate magnetic levitation.

More preferably the maglev pump configures a blood pump.

More preferably the drive unit is switchable between a mode controlling a revolution rate to be constant and a mode controlling a current to be constant and the control circuit controls a revolution rate to be substantially constant when one of the modes is switched to the other of the modes.

Furthermore the control circuit controls a revolution rate within a tolerance of approximately ±20% when one of the modes is switched the other of the modes.

Furthermore the pump includes an adjustment circuit adjusting the position of the rotative member as the rotative member levitates after the maglev pump has been assembled.

The adjustment circuit periodically moves the rotative member in the casing axially.

Furthermore the adjustment circuit includes: a periodical signal generation circuit generating a periodical signal of a low frequency and applying the periodical signal to a circuit portion of the controlled magnetic bearing unit; and a correction circuit outputting a correction signal to the control circuit to rotate the rotative member in the casing at an axially center position, in response to the output from the position detection unit when the rotative member periodically moves according to the periodical signal output from the periodical signal generation circuit.

The periodical signal generation circuit generates a periodical signal of no more than 1 Hz to periodically move the rotative member.

The present invention in another aspect provides a maglev pump including: a pump unit having in a casing a rotative member rotated to output a fluid; a support supporting the rotative member; a drive unit rotating the rotative member; and a control circuit controlling and thus preventing the rotative member from having a revolution rate varying when a supplied power supply voltage varies while the rotative member is rotating in a mode controlling a current to be constant.

Preferably the control circuit adjusts a value of a command indicative of the mode according to the supplied power supply voltage and a feedback signal proportional to a value of a current fed to the drive unit.

More preferably the power supply voltage is supplied by switching between a direct current voltage converted from an alternating current voltage and a direct current voltage supplied from a battery.

The power supply voltage is a selected and further converted one of the direct current voltage converted from the alternating current and the direct current voltage supplied from the battery.

Still more preferably, the support is coupled with the rotative member magnetically without contacting the rotative member, and the maglev pump further includes: a position detection unit detecting a position of the rotative member as the rotative member levitates; and a controlled magnetic bearing operative in response to an output of the position detection unit to support the rotative member without contacting the rotative member.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

Figure 1B:
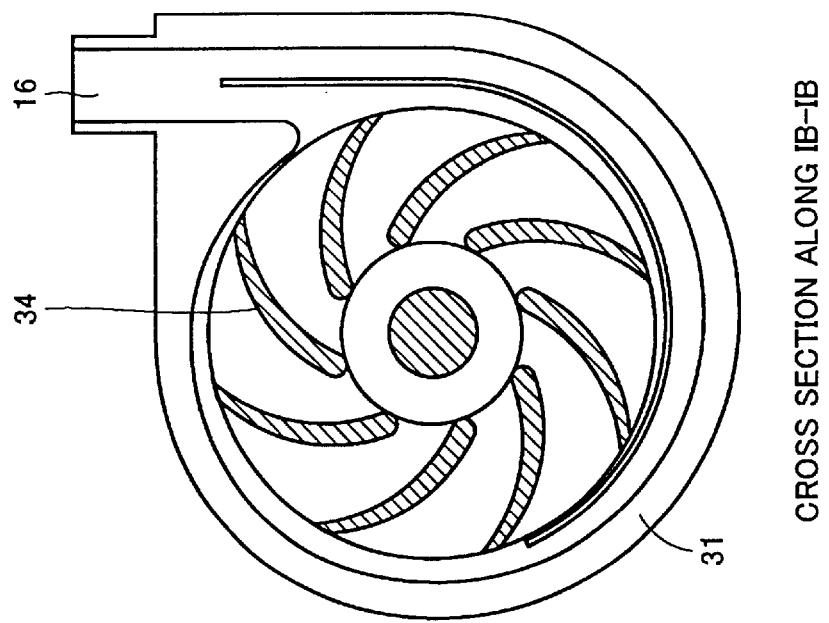
FIGS. 1A and 1B show a body of a blood pump as one embodiment of the present invention.
Figure 1A:
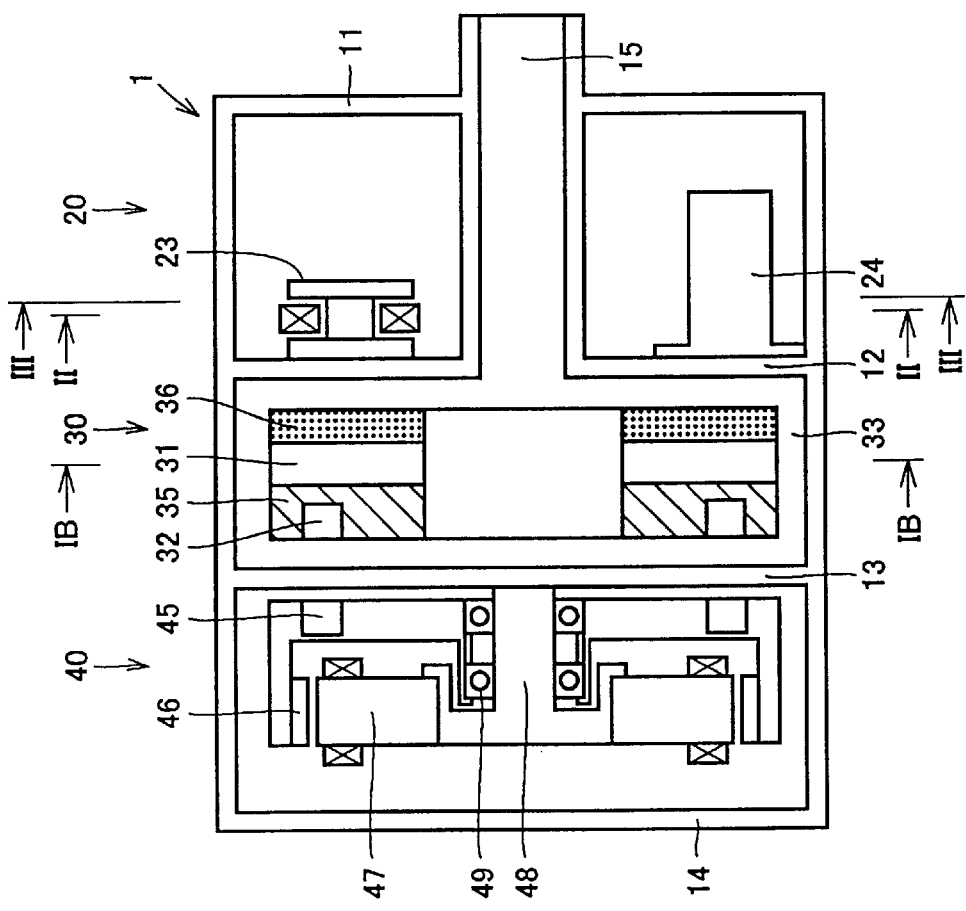
Figure 2:
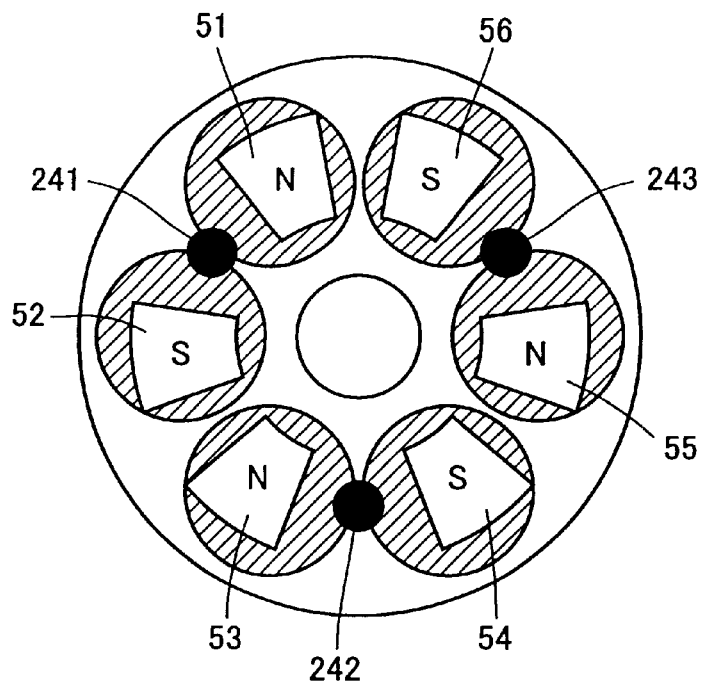
FIG. 2 is a cross section taken along line II—II of FIG. 1A.
Figure 3:
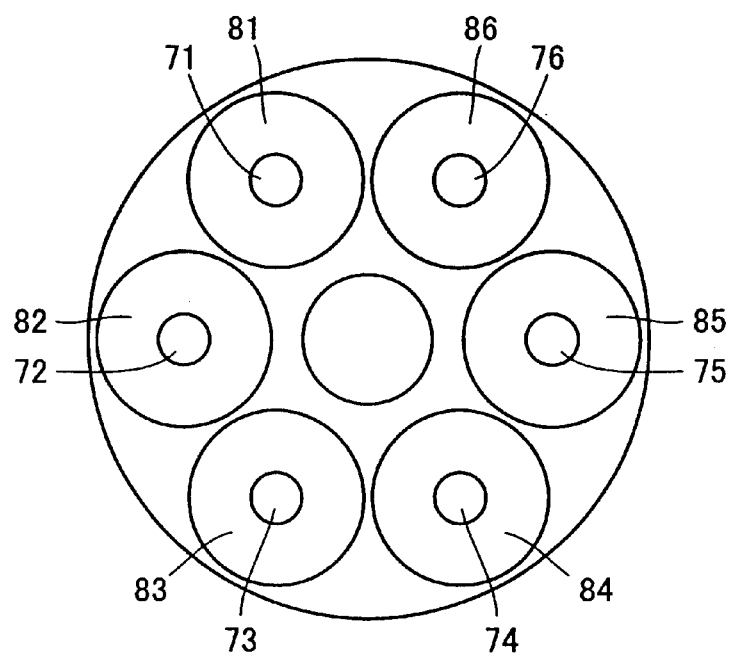
FIG. 3 is a cross section taken along line III—III of FIG. 1A.

FIGS. 1A and 1B show a body of a blood pump as one example of a maglev pump apparatus of one embodiment of the present invention. More specifically, FIG. 1A is a vertical cross section thereof and FIG. 1B is a cross section thereof taken along line IB—IB of FIG. 1A. FIG. 2 is a cross section taken along line II—II of FIG. 1A and FIG. 3 is a cross section taken along line III—III of FIG. 1A.

With reference to FIGS. 1A and 1B, the blood pump body includes a cylindrical casing 1 axially partitioned by partitions 11, 12, 13 and 14 to have sections housing a magnetic bearing unit 20, a pump unit 30 and a motor unit 40, respectively. Casing 1 is formed for example of plastic, ceramic, metal or the like, although of casing 1, partition 12 provided between electromagnet unit 20 and pump unit 30 and partition 13 provided between pump unit 30 and motor unit 40 are not allowed to be formed of magnetic material and they are accordingly formed of non-magnetic material.

At pump unit 30 casing 1 is internally provided with a pump chamber 33 in which an impeller 31 rotates to output through an outlet 16 shown in FIG. 1B a fluid introduced through an inlet 15. Impeller 31 has a plurality of vanes 34 spirally provided, as shown in FIG. 1B. Impeller 31 includes a non-magnetic member 35 having a permanent magnet 32 configuring a non-controlled magnetic bearing and a soft magnetic member 36 corresponding to a rotor of a controlled magnetic bearing. Permanent magnet 32 is divided in a circumferential direction of impeller 31 and adjacent magnets are magnetized to have opposite magnetic poles.

Note that by coating the entire interior of pump chamber 33 with heparin serving as an anticoagulant, formation of thrombus can be prevented therein and the fluid pump apparatus can thus be used as a blood delivering pump. In this example, the heparin coating can effectively limit activation of coagulation system, protect platelets, limit activation, activation of inflammation system, activation of fibrinolysis system, and the like.

In FIG. 1A, the dotted portion of impeller 31 is formed of soft magnetic material and the remainder thereof is shown formed of nonmagnetic material. If the pump is used to deliver a corrosive fluid such as blood, the soft magnetic material is preferably a highly corrosive-resistant, ferritic stainless steel (SUS447J1, SUS444 or the like) and the nonmagnetic material is preferably a highly corrosive-resistant, austenitic stainless steel (SUS316L or the like) or titanium alloy, pure titanium or the like.

Opposite to a side of impeller 31 having permanent magnet 32, a cylindrical member 48 is provided in motor unit 40, extending from a center of partition 13 toward partition 14. Cylindrical member 48 has an external peripheral surface provided with a motor bearing 49 provided in the form of a ball or roller bearing which axially supports a motor rotor 46 rotatably. Cylindrical member 48 has an end with a motor stator 47 attached thereto. Motor rotor 46 is driven by motor stator 47 to rotate. Motor rotator 46 is provided with the same number of permanent magnets 45 as permanent magnets 32 of impeller 31 opposite thereto to provide attractive force. Adjacent permanent magnets 45 are magnetized to have opposite magnetic poles.

Note that while the motor is a synchronous motor including a DC brushless motor, a non-synchronous motor including an induction motor, or the like, it may be any kind of motor.

Provided in electromagnet unit 20 are an electromagnet 23 and a position sensor 24, attached on a wall of partition 12 provided between electromagnet unit 20 and pump unit 30, opposite to that side of impeller 31 having soft magnetic member 36. Electromagnet 23 and position sensor 24 allow impeller 31 to be held at the center of pump chamber 33, matching the attractive force produced between permanent magnets 32 and 45.

Thus the heat generated at electromagnet 23 can be transferred to partition 12 and thus cooled by a fluid (blood) existing in pump unit 30. Similarly, the heat generated at motor stator 47 can also be transferred through cylindrical member 48 to partition 13 and thus cooled by the fluid existing in motor unit 30. This can reduce heat transfer to outside casing 1 and also reduce heat transfer to position sensor 24 to provide a reliable sensing operation. Furthermore, if partitions 12 and 13 are increased in thickness to have a level of strength allowing electromagnet 23, position sensor 24 and motor stator 47 to be attached thereto, housing 1 can advantageously have an outer-diameter portion reduced in thickness.

Electromagnet 23 and position sensor 24 are arranged, as shown in FIGS. 2 and 3. More specifically, paired electromagnets 23 have magnetic poles 51 and 52 with a sensor 241 arranged therebetween, magnetic poles 53 and 54 with a sensor 242 arranged therebetween, and magnetic poles 55 and 56 with a sensor 243 arranged therebetween. Sensors 241 to 243 are typically a magnetic sensor, such as a reluctance sensor.

Furthermore, as shown in FIG. 3, electromagnets 23 have their respective yokes 71–76 in the form of a column with electromagnet coils 81–86 wound therearound, respectively.

Circumferentially arranging magnetic poles 51–56 can increase the space housing electromagnet coils 81–86 that can be housed in magnetic bearing unit 40. This ensures a large space for winding the coils without increasing the size of the pump. Increasing a space for housing a coil in turn allows an electromagnet coil to have an increased turn count and an increased wire diameter and can thus save power for the electromagnet.

Furthermore, electromagnet yokes 71–76 in the form of a column can facilitate winding electromagnet coils 81–86 around electromagnet yokes 71–76, respectively. Electromagnet yokes 71–76 having a simple geometry also ensure insulation from electromagnet coils 81–86. While electromagnet yokes 71–76 are cylindrical, they may be in the form of a prism, which can facilitate winding coils and thus ensuring a withstand voltage between the coils and the yokes.

Furthermore while in FIGS. 2 and 3 electromagnet yokes 71–76 and electromagnet coils 81–86 are all arranged in a single circle, they may not thus be arranged, if required, to effectively ensure a space for housing the same.

With the magnetic bearing having each electromagnet with its magnetic pole and yoke arranged circumferentially, the magnetic bearing unit is not required to have a large space and the electromagnet yoke can be provided in a cylinder or a prism, which can facilitate winding coils and thus ensuring a withstand voltage between the coils and the yokes.

Figure 4:
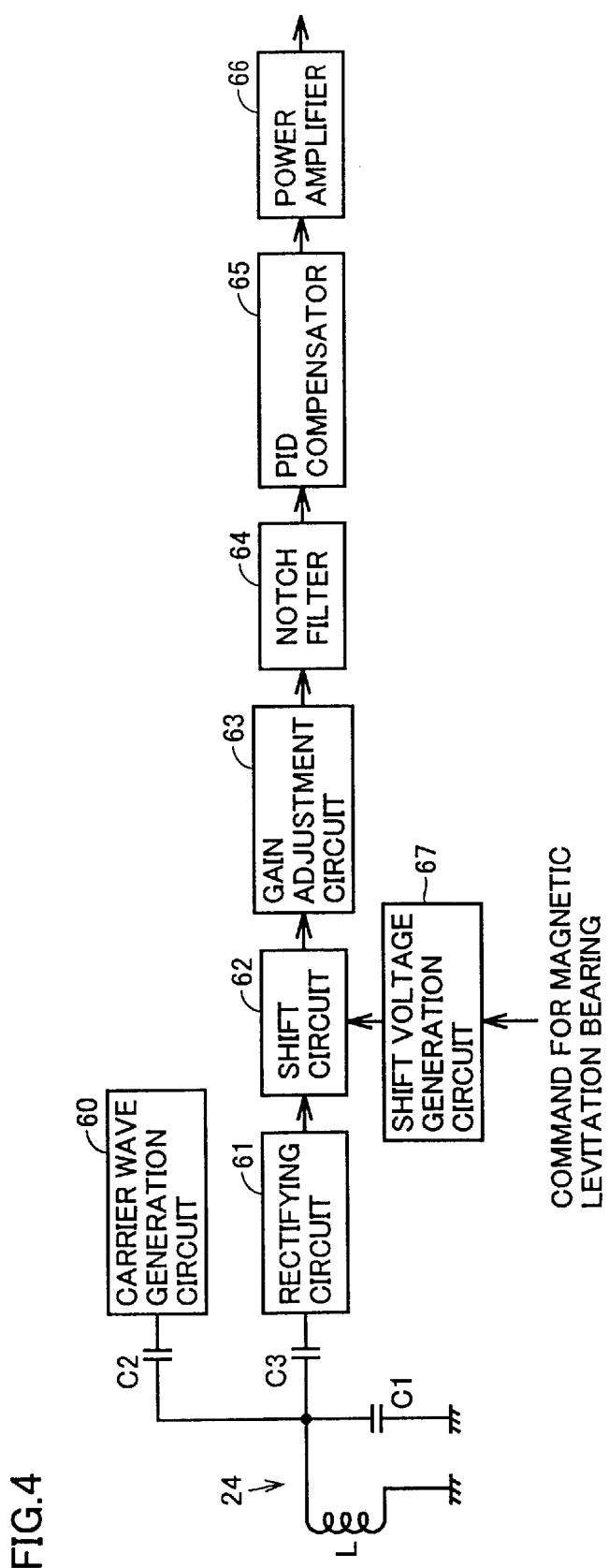
FIG. 4 is a schematic block diagram showing one embodiment of a controller controlling the body of the blood pump shown in FIGS. 1A and 1B.

FIG. 4 is a block diagram showing an example of a controller controlling a blood pump of the embodiment shown in FIGS. 1A and 1B.

In FIG. 4, the FIGS. 1A and 1B position sensor 24 has an inductance L and receives a carrier wave signal for example of 100 kHz from a carrier wave generation circuit 60 via a capacitor C2. Position sensor 24 outputs via a capacitor C3 to a rectifying circuit 61 a detection signal with the carrier wave having an amplitude varying as the distance from the FIGS. 1A and 1B impeller 31 varies. Rectifying circuit 61 rectifies the detection signal to provide a dc signal which is in turn output to a shift circuit 62.

In magnetic levitation, shift circuit 62 compulsively sets an output of position sensor 24 to allow impeller 31 to have a position closer to motor 40 as the impeller levitates. More specifically, shift circuit 62 raises the sensor output according to a shift voltage applied from a shift voltage generation circuit 67 to gradually, magnetically levitate impeller 31. Shift voltage generation circuit 67 responds to a command to provide magnetic bearing levitation by outputting and supplying a shift voltage to shift circuit 62. A gain adjustment circuit 63 adjusts a gain. The sensor signal with the gain adjusted is fed to a notch filter 64 and the carrier wave thus has a center frequency component removed.

Figure 5:
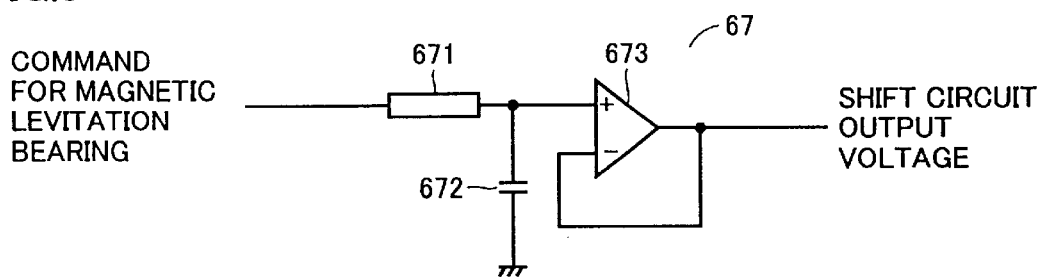
FIG. 5 shows a shift voltage generation circuit shown in FIG. 4.

FIG. 5 shows an example of the FIG. 4 shift voltage generation circuit. In the figure, a signal corresponding a command to levitate the impeller via the magnetic bearing, is input via a resistance 671 to an operational amplifier 673 at a non-inverting input. Between the non-inverting input and ground is connected a capacitor 672. Operational amplifier 673 also has an inverting input and an output terminal connected to the inverting input and outputting a shift voltage.

Figure 6:
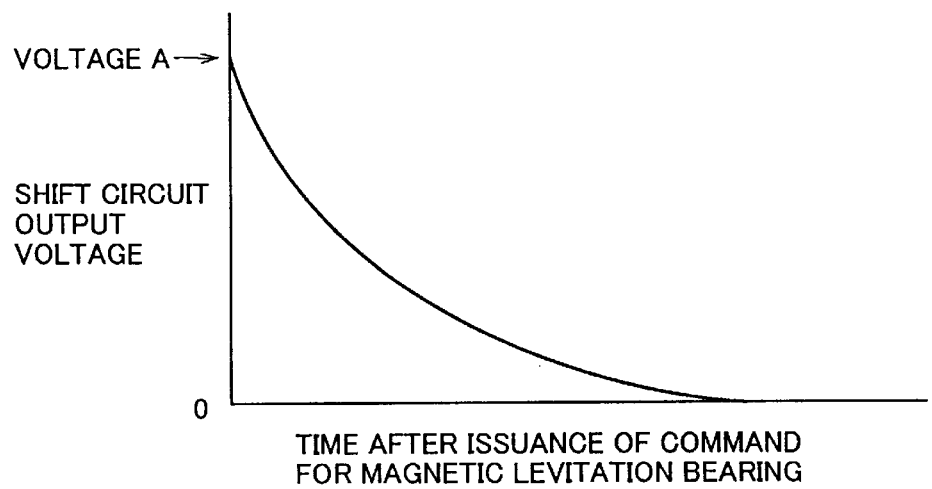
FIG. 6 represents a shift circuit output voltage varying with time after a command is issued to provide magnetic levitation.
Figure 7:
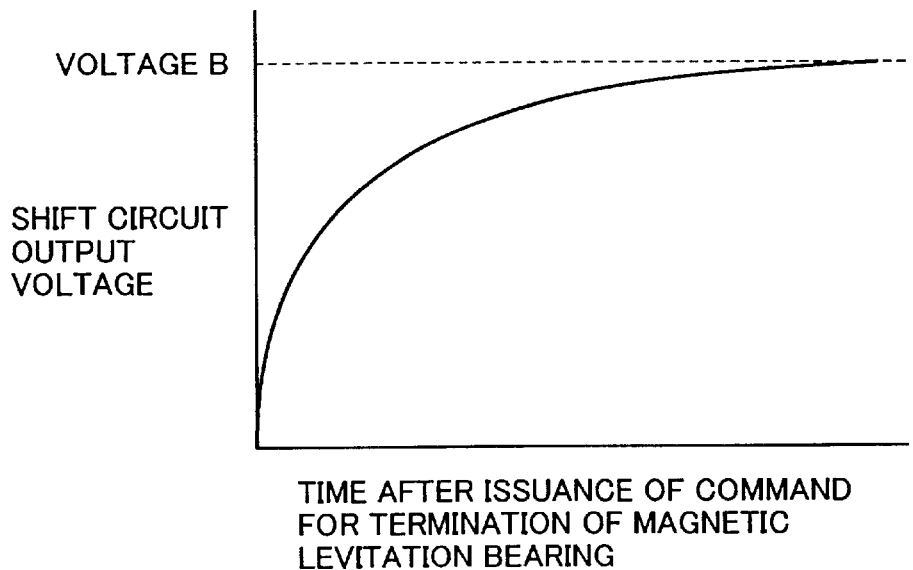
FIG. 7 represents a shift circuit output voltage varying with time after a command is issued to terminate magnetic levitation.
Figure 8:
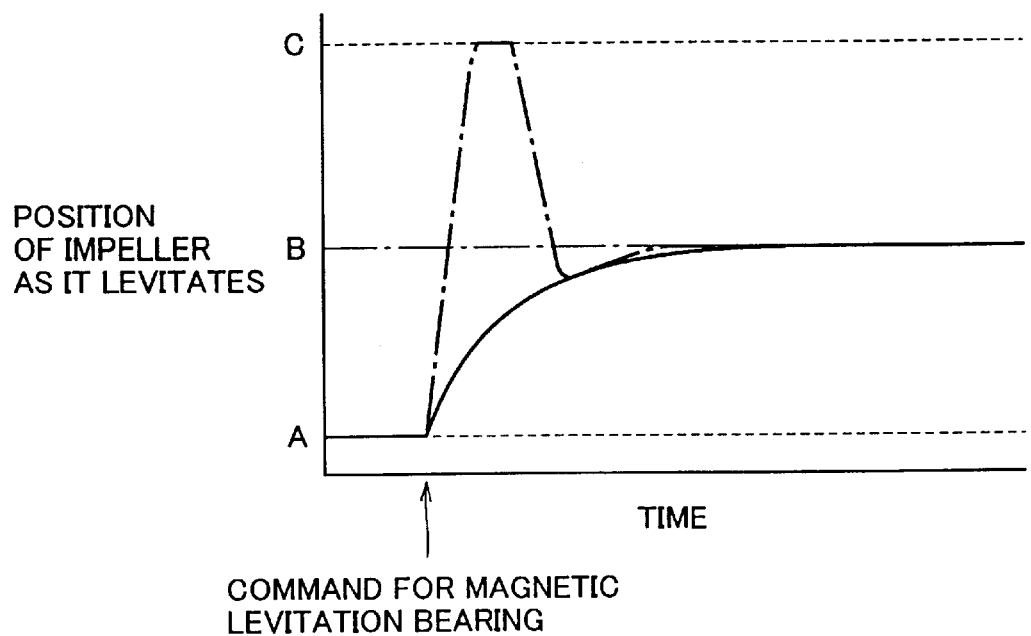
FIG. 8 represents the position of the impeller varying with time as the impeller levitates after a command is issued to provide magnetic levitation.

FIG. 6 represents the shift circuit output voltage varying with time after a command is issued to terminate the impeller's levitation via the magnetic bearing. FIG. 7 represents the shift circuit output voltage varying with time after a command is issued to stop levitating the impeller via the magnetic bearing. FIG. 8 represents the position of the impeller varying with time as the impeller levitates.

In FIG. 5, when the command signal to provide magnetic levitation goes high the magnetic levitation is terminated and when the command signal is driven low the magnetic levitation is provided. When the command signal is driven low, electric charge stored in capacitor 672 is discharged and the operational amplifier 673 output, corresponding to the shift circuit output voltage, gradually reduces, as shown in FIG. 6. The shift circuit output voltage is composited with a voltage output from a rectifying circuit 61. Thus shift circuit 62 outputs a gradually increasing voltage to gain adjustment circuit 63. Consequently, impeller 31 can be free from conventional overshoot when it levitates, and, as represented in FIG. 8 by the solid line, as time elapses the impeller gradually levitates from position A corresponding to an inner wall surface of motor unit 40 and arrives at normal position B. This can prevent magnetically levitated impeller 31 from impinging against and damaging an inner wall of pump chamber 33.

When the signal indicating the command to provide magnetic levitation goes high to terminate magnetic levitation, capacitor 672 is charged via resistance 671 and operational amplifier 673 thus outputs a voltage gradually increasing as shown in FIG. 7. Consequently, shift circuit 62 outputs a gradually decreasing voltage to gain adjustment circuit 63. Consequently impeller 31 moves gradually from normal position B shown in FIG. 8 to position A corresponding to an internal wall surface closer to motor unit 40 and stops there.

Thus in the present embodiment when the rotative member is to be magnetically levitated a command is issued to allow the rotative member to have a position closer to the drive unit as it levitates. Thus the rotative member can be free of overshooting and thus prevented from moving from a position closer to the drive unit toward the controlled magnetic bearing and impinging against and thus damaging an internal wall of the housing.

Figure 18:
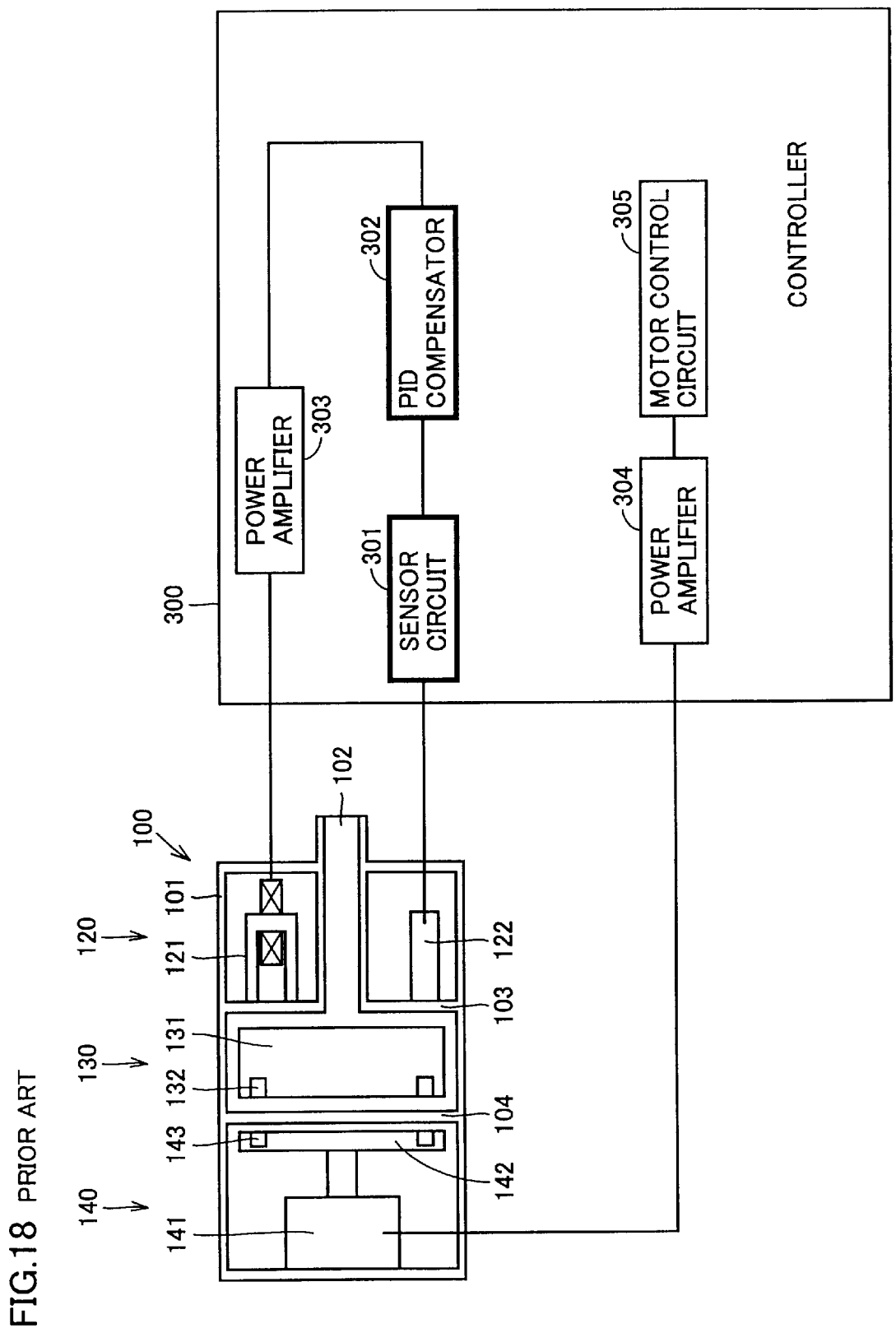
FIG. 18 shows a conventional maglev pump apparatus and controller.
Figure 19:
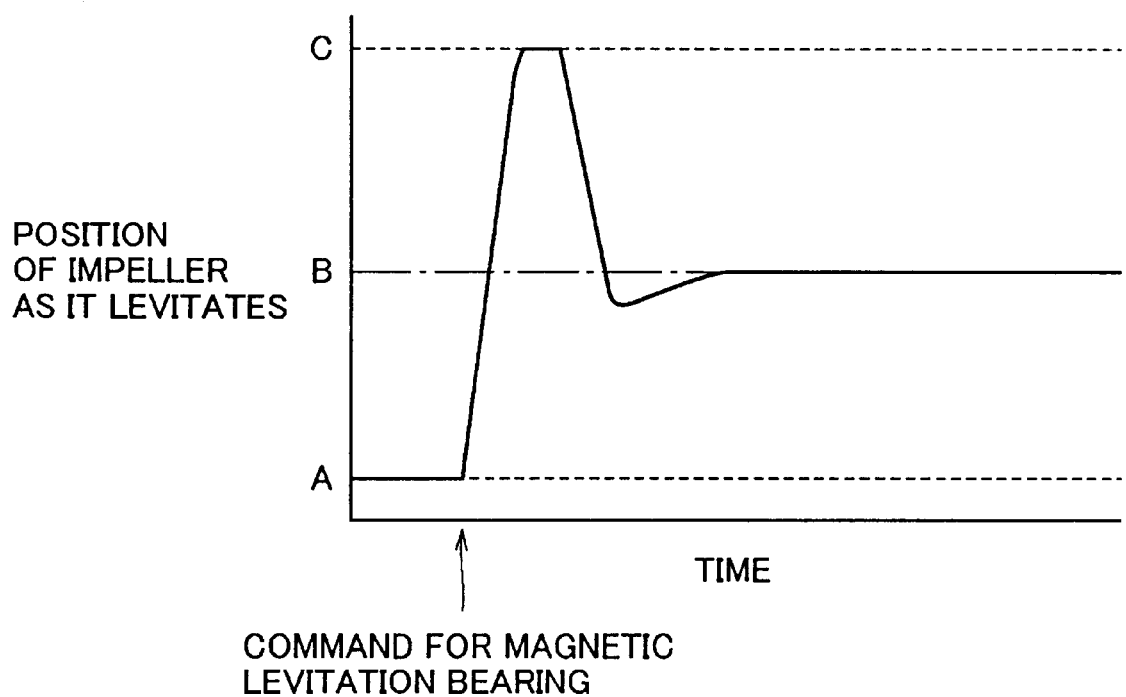
FIG. 19 represents the position of an impeller varying with time as it levitates after a command is issued to provide magnetic levitation.

The FIG. 18 maglev fluid pump 100 is used as a blood pump for an artificial heart, and controller 300 can switch motor 140 between a constant revolution rate (CRR) mode and a constant motor current (CMC) mode. In the CRR mode if a motor is revolving for example at a rate of 2000 rpm and a load imposed varies the motor still can rotate at the same, constant revolution rate. The CMC mode allows a motor to pass a constant current for example of 1A. In the CMC mode, a blood pump has a revolution rate increasing to supply a constant amount of blood when a blood vessel contracts, and the blood pump has a revolution rate decreasing when the blood vessel expands as a load imposed thereon is reduced. However, if in use a mode is switched to another and for example an erroneous operation results in a motor revolution rate varying significantly the pump's load system may be disadvantageously overloaded.

A description will now be provided of an embodiment capable of preventing a revolution rate from significantly varying when a mode is switched to another.

Figure 9:
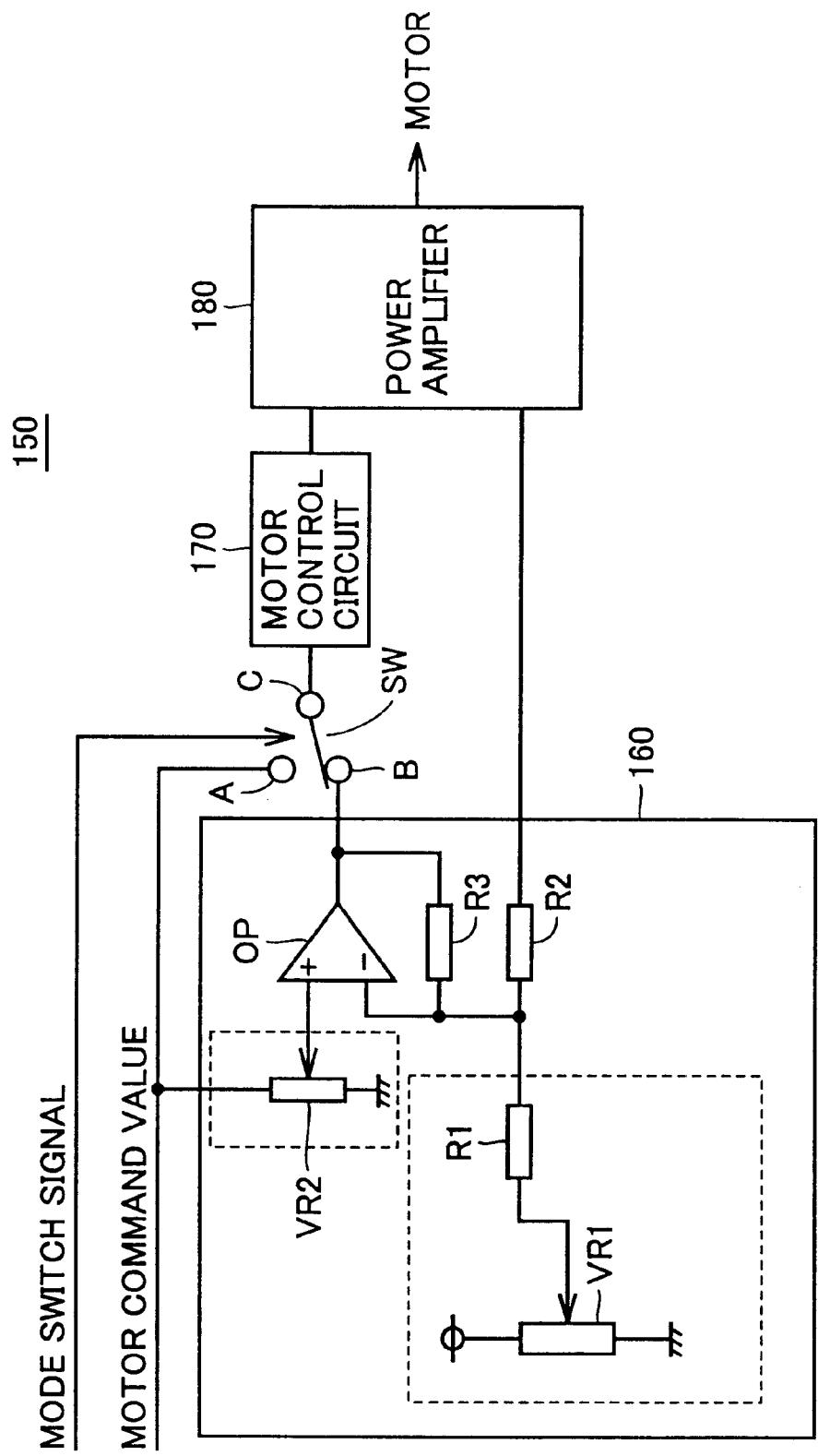
FIG. 9 is a block diagram showing a controller controlling a maglev pump apparatus provided as another embodiment of the present invention.

FIG. 9 is a block diagram showing a controller controlling a maglev pump apparatus of such an embodiment. A blood pump with the present invention applied thereto normally revolves in a range of 1500 rpm to 2500 rpm and seldom rotates at a rate higher or lower than this range. Accordingly, in the present embodiment, a relationship between current and revolution rate is calculated with a predetermined revolution rate range adopted, to control the pump to revolve at a constant rate if one mode is switched to another. Such control is implemented by a controller 150 as shown in FIG. 9.

In FIG. 9, controller 150 includes a mode conversion adjustment circuit 160, a motor control circuit 170, a power amplifier 180 and a mode switch SW. Motor control circuit 170 provides control to maintain a constant value of a motor revolution rate corresponding to the value of a signal input thereto and it is provided in the form of a motor revolution rate control circuit. Power amplifier 180 is provided to supply power to the motor in response to an output of motor control circuit 170.

A mode switch signal is provided to switch between the CRR mode and the CMC mode and it switches mode switch SW. More specifically, as shown in FIG. 9, mode switch SW has contact points A and C connected together in the CRR mode and contact points B and C connected together in the CMC mode.

Via mode switch SW motor control circuit 170 receives a signal, which corresponds to a motor revolution rate command value. More specifically, if in response to a mode switch signal mode switch SW has connection points A and C connected together then a motor command value serves as a motor revolution rate command value and the motor is controlled to have a revolution rate in proportion to the command value (the CRR mode).

The motor command value allows the FIG. 1A motor 40 to rotate in the CRR mode and it is also applied to mode conversion adjustment circuit 160. Mode conversion adjustment circuit 160 converts the motor command value to a constant motor current (CMC) value, i.e., a value allowing motor 40 to have a revolution rate free of significant variation when a mode switches to another.

Mode conversion adjustment circuit 160 is an operation circuit added receiving and allowing a motor command value to control a motor current to have a constant value and it is configured to prevent motor 40 from having a significantly varying revolution rate when a mode switches to another. More specifically, mode conversion adjustment circuit 160 includes variable resistances VR1 and VR2, an operational amplifier OP, and resistances R1–R3. A motor command value is divided by variable resistance VR2 to have a gain adjusted. Operational amplifier OP has a non-inverting input receiving the motor command value divided by variable resistance VR2, and an inverting input receiving a voltage in proportion to a motor current via resistance R2 and also receiving via resistance R1 a voltage set by variable resistance VR1. More specifically, mode conversion adjustment circuit 160 feeds an amount of motor current back to operational amplifier OP to function to provide an operation to obtain a signal to be input to motor control circuit 170 so as to obtain a motor current corresponding to a motor command value. Resistance R3 is provided to adjust a gain for the entirety of operational amplifier OP.

If in response to a mode switch signal mode switch SW has connection points B and C connected together then an output of mode conversion adjustment circuit 160 controls the motor and the CMC mode is thus set.

Figure 10:
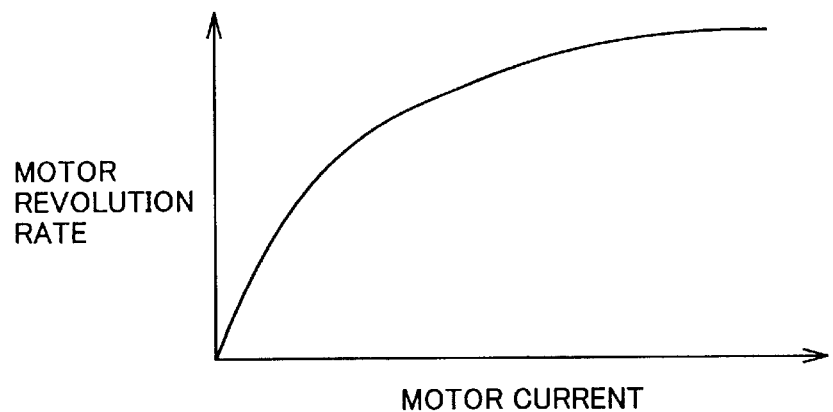
FIG. 10 represents a relationship between motor revolution rate and motor current when the FIG. 9 pump is used as a blood pump.

FIG. 10 represents a relationship between motor revolution rate and motor current when the FIG. 1A pump is used as a blood pump. As shown in the figure, when a current starts to flow a motor revolution rate also increases accordingly, although the motor revolution rate and the motor current are not in proportion to each other. However, the blood pump has a range of revolution rate normally used and therein a motor revolution rate and a motor current can approximate linearly.

Figure 11:
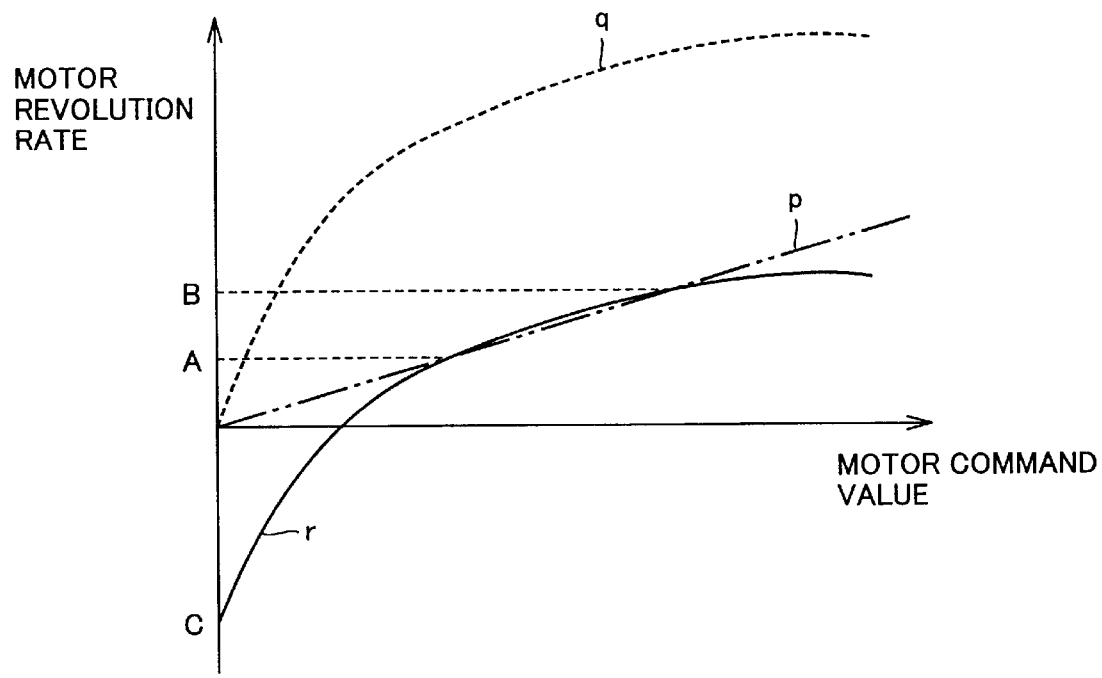
FIG. 11 represents a relationship between motor command value and motor revolution rate.

FIG. 11 represents a relationship between a motor command value and a motor revolution rate. In the figure, a chained line represents the relationship in the CRR mode, a broken line q represents the relationship when neither VR2 functioning to adjust a gain in mode conversion adjustment circuit 160 nor VR1 providing operational amplifier OP's offset adjustment are adjusted, and a solid line r represents the relationship matching that in the CRR mode within a normal motor revolution rate range of A to B as VR1 an VR2 are adjusted.

Thus there can be shown that at a normal revolution rate the motor's revolution can have a variation range limited for a single given motor command value in both of the CRR mode and the CMC mode. In FIG. 11, for solid line r, an intercept c on axis y can be adjusted with variable resistance VR1 (in mode conversion adjustment circuit 160) and the gradient between motor revolution rate A–B can be adjusted with variable resistance VR2 (in mode conversion adjustment circuit 160).

In the FIG. 11 solid line r adjustment preferably the blood pump's standard condition for use is previously assumed and a relationship between the impeller 31 revolution rate and motor current is previously obtained in a pump load system using a blood vessel having a length and diameter to be actually used, to allow a motor command value to control a revolution rate to be substantially uniform in the two modes. Practically, it is tolerable if the uniform revolution rate is achieved within a range of approximately ±20%.

Thus when mode switch SW switches a mode to the CMC mode a motor command value is converted to a linear line p shown in FIG. 11 and the converted output is fed from operational amplifier OP to motor control circuit 170 which in turn provides an output which is received by power amplifier 180 to drive motor stator 47.

Thus in the present embodiment if the CRR mode and the CMC mode are switched the both modes can maintain substantially the same revolution rate to prevent the pump load system of interest from bearing a disadvantageous overload.

Thus in the present embodiment when the both modes of constant revolution rate control and constant current control are switched a revolution rate can be controlled to have a substantially constant value to prevent the pump load system of interest from bearing a disadvantageous overload when the modes are switched.

If maglev pump apparatus 100 is used as an artificial heart, casing 101 has each portion welded and thus assembled to seal pump unit 130 airtight. As such, after it is assembled the casing cannot be disassembled and accordingly impeller 131 and position sensor 122 cannot have a distance therebetween that is adjustable. A description will now be provided of an embodiment of a maglev pump apparatus capable of adjusting the position of the rotative member as it rotates so that the sensor output can be optimized after the casing is assembled.

Figure 12:
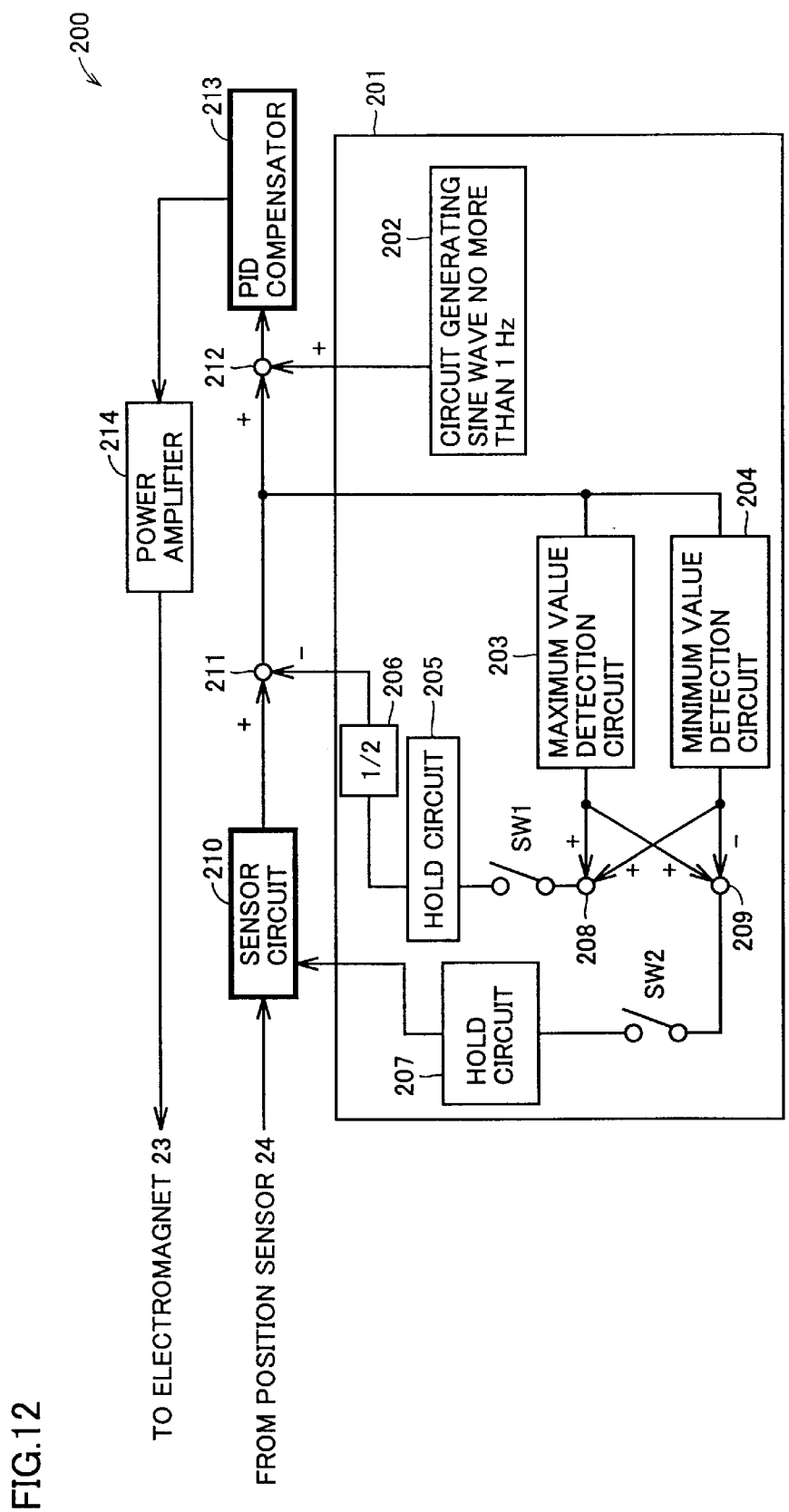
FIG. 12 is a block diagram showing an exemplary controller controlling a maglev pump apparatus provided as still another embodiment of the present invention.

FIG. 12 is a block diagram showing a controller controlling a maglev pump apparatus of such an embodiment.

In FIG. 12 a controller 200 includes a sensor adjustment circuit 201, a sensor circuit 210, addition circuits 211 and 212, a PID compensator 213, and a power amplifier 214. Sensor adjustment circuit 201 includes a sine wave generation circuit 202 generating a sine wave signal serving as a periodical signal of no more than 1 Hz, such as 0.5 Hz, and inputting the signal to addition circuit 212 provided at a stage preceding PID compensator 213. Addition circuit 212 receives the sensor output and adds thereto a sine wave of 0.5 Hz and outputs it to PID compensator 213.

The sensor output is also fed to a maximum value detection circuit 203 and a minimum value detection circuit 204. Maximum value detection circuit 203 detects a maximum value of the sensor output and minimum value detection circuit 204 detects a minimum value of the sensor output. The output of maximum value detection circuit 203 and that of minimum value detection circuit 204 are input to addition circuits 208 and 209. Addition circuit 208 adds the maximum and minimum values together and addition circuit 209 extracts the minimum value from the maximal value. Thus addition circuit 208 outputs an average value of the maximum and minimum values in amplitude of the sensor output and addition circuit 209 outputs a difference between the maximum and minimum values, i.e., an amplitude.

The addition circuit 208 output is fed via a switch element SW1 to a hold circuit 205 which provides an output received by a ½ circuit 206 and thus halved and thus fed to addition circuit 211. The amplitude output from addition circuit 209 is fed via a switch element SW2 to a hold circuit 207 which provides an output received by sensor circuit 210 as a signal to correct a gain of a sensor output.

Sensor circuit 210 receives a sensor output from position sensor 24 and it receives the output of hold sensor 207 to adjust a gain of the sensor. The sensor circuit 210 output is input to addition circuit 211 and the addition circuit 211 output is input to addition circuit 212.

Figure 13:
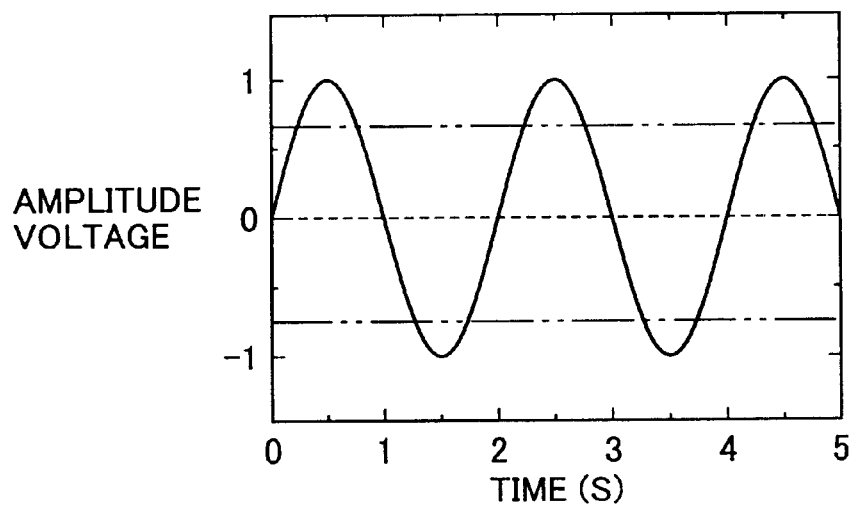
FIG. 13 is a waveform diagram of a sine wave output from the sine wave generation circuit shown in FIG. 12.
Figure 14:
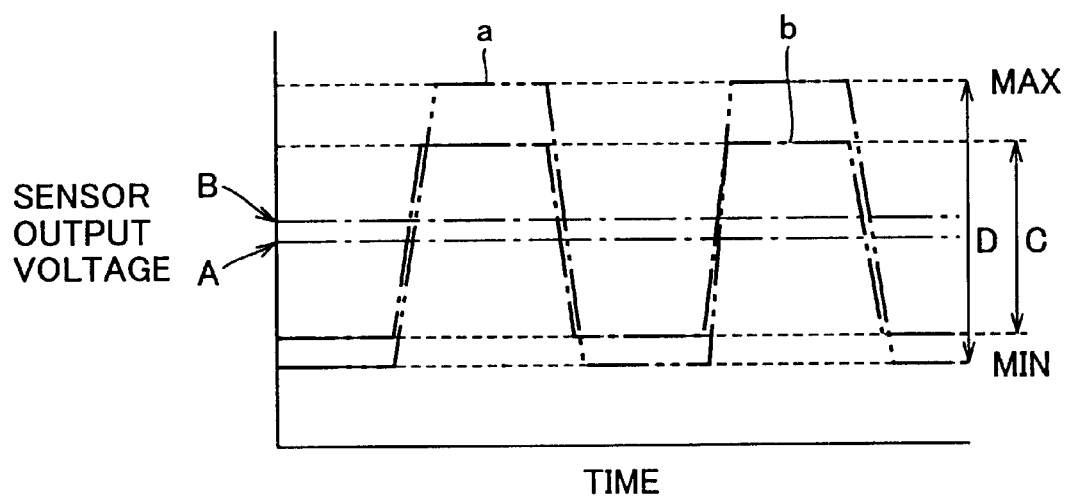
FIG. 14 represents a relationship between sensor output and time.

FIG. 13 is a waveform diagram of a sine wave output from the FIG. 12 sine wave generation circuit 202 and FIG. 14 represents a relationship between sensor output and time.

With reference to FIGS. 12–14 an operation of the present embodiment will be described. Sine wave generation circuit 202, as shown in FIG. 13, generates a sine wave signal of no more than 1 Hz, such as 0.5 Hz. This sine wave signal is added to a sensor output by addition circuit 212, which in turn outputs the addition to PID compensator 213 for PID-compensation and then amplified by power amplifier 214 which outputs a drive signal to drive the FIG. 1 electromagnet 23. The signal driving electromagnet 23 has an amplitude varying in synchronization with a waveform shown in FIG. 13, owing to the 0.5 Hz sine wave signal.

As such electromagnet 23 exerts attractive force toward impeller 31 that is intensified and weakened in a cycle of 0.5 Hz and impeller 31, as shown in FIG. 1A, moves between partition 12 closer to electromagnet unit 20 and partition 13 closer to motor 40 in pump chamber 33 in the axial direction slowly, repeatedly. Depending on the level of the sine wave signal, impeller 31 can abut against an internal wall of pump chamber 33 However, impeller 31 moves depending on the 0.5 Hz sine wave and thus does not impinge against an internal wall of pump chamber 33 to damage the heparin coating the wall surface.

As impeller 31 is moved by the 0.5 Hz sine wave signal axially, the position sensor 24 output also varies significantly, and maximum and minimum value detection circuits 203 and 204 detect maximum and minimum values, respectively, of the voltage of the sensor output. The detected maximum and minimum values are added together by addition circuit 208 and addition circuit 209 also subtracts the minimum value from the maximum value. The maximum and minimum values have a relationship as shown in FIG. 14. More specifically, sensor circuit 210 outputs a voltage in a waveform a having an amplitude D between MAX and MIN shown in FIG. 14. FIG. 14 also represents a waveform b corresponding to set data having an amplitude C and a neutral voltage as indicated by A in FIG. 6. In FIG. 14, MAX represents impeller 31 closest to magnetic bearing unit 20 and MIN represents impeller 31 closest to motor unit 40.

The addition circuit 208 output is fed via switch element SW1 to hold circuit 205 and held therein. Hold circuit 205 provides an output received by ½ circuit 206 and thus halved and then fed to addition circuit 211. The addition circuit 211 input corresponds to the FIG. 14 voltage B. The addition circuit 209 output is fed via switch element SW2 to hold circuit 207 and held therein. The hold voltage is applied to sensor circuit 210 to correct a gain of sensor circuit 210. More specifically, the ½ circuit 206 output allows impeller 31 to levitate in pump chamber 33 at a neutral position, as set in addition circuit 211, while the hold circuit 207 output corrects a gain of a sensor output. Consequently, impeller 31 can have the neutral position that corresponds to the FIG. 14 voltage A and furthermore the sensor output's voltage can have a gain set to have a value as desired.

Note that the above setting is provided as follows: with electromagnet 23 and motor unit 40 driven to magnetically levitate impeller 31, sine wave generation circuit 202 is operated to generate a sine wave and then when for example a temporal period of 10 seconds has elapsed the generation of the sine wave is stopped and switch elements SW1 and SW2 are turned on.

Consequently, if impeller 31 is sealed in pump chamber 33 its neutral position can be set to obtain an appropriate sensor output.

While in the above description sine wave generation circuit 202 generates a sine wave of 0.5 Hz, any frequency no more than 1 Hz is applicable to the present invention.

Figure 15:
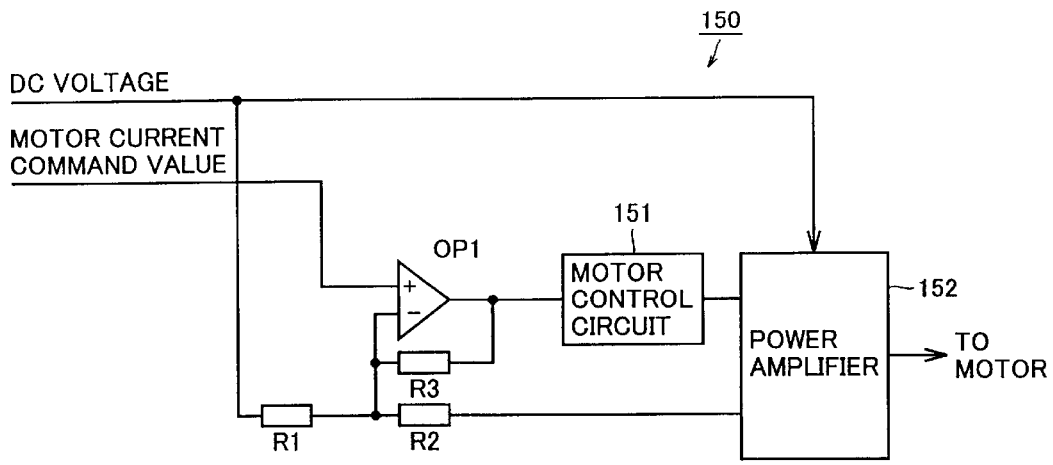
FIG. 15 is a block diagram showing an exemplary controller controlling a blood pump apparatus provided as still another embodiment of the present invention.
Figure 16:
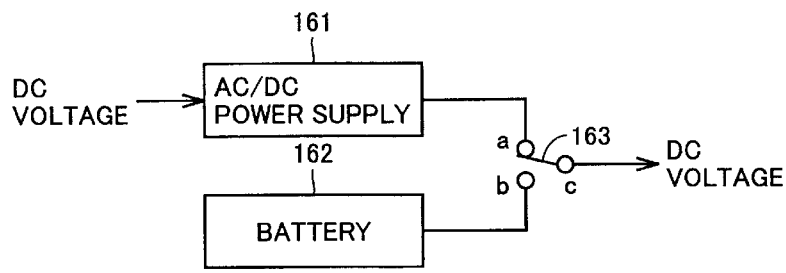
FIG. 16 shows an exemplary power supply circuit supplying the FIG. 15 power amplifier with a power supply voltage.
Figure 17:
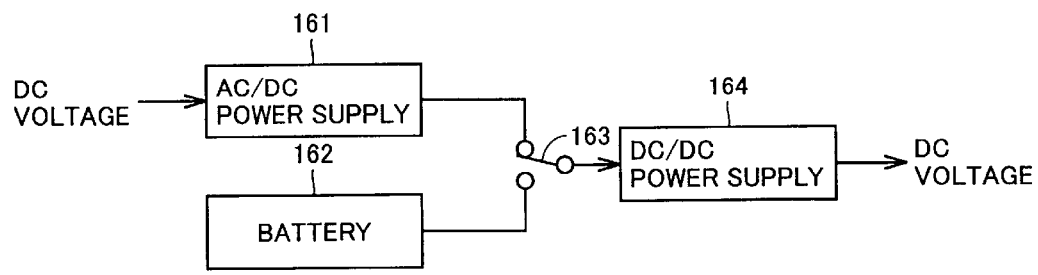
FIG. 17 shows another exemplary power supply circuit supplying the FIG. 15 power amplifier with a power supply voltage.

FIG. 15 is a block diagram showing an example of a controller controlling a blood pump apparatus in a still another embodiment of the present invention, and FIGS. 16 and 17 show a power supply circuit supplying the FIG. 15 power amplifier with a power supply voltage.

A blood pump with the present invention applied thereto normally revolves in a range of 1500 rpm to 2500 rpm and seldom revolves at a rate higher or lower than this range. Accordingly, in the present embodiment, a relationship between a power supply voltage and a motor current command value is calculated in a predetermined revolution rate range to control the motor current command value to allow the pump to revolve at a constant rate if power supply voltage varies. Such control is implemented by a controller 150 as shown in FIG. 15.

In FIG. 15, controller 150 includes a motor control circuit 151, a power amplifier 152, an operational amplifier OP1, and resistances R1, R2, R3. Power amplifier 152 drives the FIG. 1A motor unit 40 and in response to a control signal from motor control circuit 151 supplies motor stator 47 with a predetermined direct current.

Power amplifier 152 receives a dc voltage from the FIG. 16 or 17 power supply circuit. In the FIG. 16 example, a commercial ac voltage is converted by an AC/DC power supply 161 to a dc voltage, more preferably a stable dc voltage, which is fed to a switch 163 at a contact point a, while a battery 162 feeds a dc voltage to switch 163 at a contact point b. Switch 163 is switched to allow a contact point c to output a dc voltage which is in turn fed to power amplifier 152.

In the FIG. 17 example, the dc voltage from AC/DC power supply 161 and that from battery 162 are switched by switch 163 and furthermore boosted or down-converted by a DC/DC power supply 164 such as an inverter power supply before it is fed to power amplifier 152. If DC/DC power supply 164 is employed and when the battery 162 charge voltage varies, a dc voltage output may also vary.

Power amplifier OP1 has a non-inverting input receiving a motor current command value and an inverting input receiving a dc voltage via resistance R1. The operational amplifier OP1 inverting input also receives a feedback signal from power amplifier 152 via resistance R2 and a signal output from operational amplifier OP1 via resistance R3. The operational amplifier OP1 output signal is applied to motor control circuit 151.

The present embodiment specifically operates, as described below. For the sake of convenience, the FIG. 16 AC/DC power supply 161 feeds a dc 12V voltage to power amplifier 152, a motor current command value of 1A is set and the motor has a revolution rate of 1500 rpm.

When switch 163 is switched to the dc voltage of battery 162 and if battery 162 is fully charged and dc voltage is for example 15V then power amplifier 152 operates to increase the motor's revolution rate. However, the dc voltage is received via resistance R1 by operational amplifier OP1 at the inverting input, and as the dc voltage increases from 12V to 15V operational amplifier OP1 has the inverting input increased in potential and thus operates to decrease its output signal, or a motor current command value, in level. In response to the motor current command value motor control circuit 151 controls the motor's revolution, resulting in the motor having a reduced revolution rate.

In contrast, when dc voltage is lower than a rated voltage and if a motor current command value is a constant value then the motor's revolution rate reduces. However, the operational amplifier OP1 inverting input also has a voltage reduced and operational amplifier OP1 operates to increase its output signal in level. Consequently, operational amplifier OP1 outputs a signal larger in level than the motor current command value and in response to the motor current command value motor control circuit 151 increases the motor's revolution rate.

Thus in the present embodiment if dc voltage is higher or lower than a rated voltage a motor current command value can be decreased or increased to prevent dc voltage variation from resulting in a motor revolution rate having a significant variation.

Note that while in the above embodiment the present invention is applied to a maglev blood pump apparatus by way of example it is applicable to any blood pump apparatus controlled in response to a motor current command value to have a constant motor revolution rate.

Thus, in the present embodiment, in a mode controlling a current to be constant, allowing a drive unit to receive a constant current to rotate a rotative member, if a power supply voltage varies a revolution rate can be controlled to be free of variation for example to prevent a pump load system from disadvantageously bearing an overload.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. A maglev pump, comprising:
   a pump unit outputting a fluid through revolution of a rotative member in a casing;
   a drive unit magnetically coupled with said rotative member without contacting said rotative member, to rotate said rotative member;
   a position detection unit detecting a position of said rotative member as said rotative member levitates;
   a controlled magnetic bearing unit operative in response to an output of said position detection unit to support said rotative member without contacting said rotative member; and
   a control circuit controlling a command signal of said controlled magnetic bearing unit to allow said rotative member to have a position closer to said drive unit when said rotative member starts magnetic levitation.

2. The maglev pump of claim 1, wherein in magnetic levitation said control means shifts the output of said position detection unit gradually to a normal value.

3. The maglev pump of claim 1, wherein to terminate magnetic levitation said control means changes the output of said position detection unit gradually from said normal value to shift the position of said rotative member toward said pump unit as said rotative member levitates.

4. The maglev pump of claim 3, wherein said maglev pump configures a blood pump.

5. The maglev pump of claim 1, wherein:
    said drive unit is switchable between a mode controlling a revolution rate to be constant and a mode controlling a current to be constant; and
    said control circuit controls a revolution rate to be substantially constant when one of said modes is switched to the other of said modes.

6. The maglev pump of claim 5, wherein said control circuit controls a revolution rate within a tolerance of approximately ±20% when one of said modes is switched the other of said modes.

7. The maglev pump of claim 5, wherein said maglev pump configures a blood pump.

8. The maglev pump of claim 1, further comprising an adjustment circuit adjusting the position of said rotative member as said rotative member levitates after said maglev pump has been assembled.

9. The maglev pump of claim 8, wherein said adjustment circuit periodically moves said rotative member in said casing axially.

10. The maglev pump of claim 9, wherein said adjustment circuit includes:
    a periodical signal generation circuit generating a periodical signal of a low frequency and applying said periodical signal to a circuit portion of said controlled magnetic bearing unit; and
    a correction circuit outputting a correction signal to said control circuit to rotate said rotative member in said casing at an axially center position, in response to the output from said position detection unit when said rotative member periodically moves according to said periodical signal output from said periodical signal generation circuit.

11. The maglev pump of claim 10, wherein said periodical signal generation circuit generates a periodical signal of no more than 1 Hz to periodically move said rotative member.

12. The maglev pump of claim 11, wherein said maglev pump configures a blood pump.

13. A maglev pump comprising:
    a pump unit having in a casing a rotative member rotated to output a fluid;
    a support supporting said rotative member;
    a drive unit rotating said rotative member; and
    a control circuit controlling and thus preventing said rotative member from having a revolution rate varying when a supplied power supply voltage varies while said rotative member is rotating in a mode controlling a current to be constant.

14. The maglev pump of claim 13, wherein said control circuit adjusts a value of a command indicative of said mode according to said supplied power supply voltage and a feedback signal proportional to a value of a current fed to said drive unit.

15. The maglev pump of claim 14, wherein said power supply voltage is supplied by switching between a direct current voltage converted from an alternating current voltage and a direct current voltage supplied from a battery.

16. The maglev pump of claim 15, wherein a selected one of the direct current voltage converted from the alternating current and the direct current voltage supplied from the battery, is further converted to provide said power supply voltage.

17. The maglev pump of claim 13, said support being coupled with said rotative member magnetically without contacting said rotative member, further comprising:
    a position detection unit detecting a position of said rotative member as said rotative member levitates; and
    a controlled magnetic bearing operative in response to an output of said position detection unit to support said rotative member without contacting said rotative member.

* * * * *